(12) United States Patent
Man et al.

(10) Patent No.: US 7,345,062 B2
(45) Date of Patent: *Mar. 18, 2008

(54) SUBSTITUTED ACYLHYDROXAMIC ACIDS AND METHOD OF REDUCING TNFαLEVELS

(75) Inventors: Hon-Wah Man, Princeton, NJ (US); George W Muller, Bridgewater, NJ (US); Shaei Y Huang, Jeffersonville, PA (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/786,822

(22) Filed: Feb. 25, 2004

(65) Prior Publication Data

US 2004/0167174 A1     Aug. 26, 2004

Related U.S. Application Data

(62) Division of application No. 09/468,529, filed on Dec. 21, 1999, now Pat. No. 6,699,899.

(51) Int. Cl.
*A61P 35/00*     (2006.01)
*A61K 31/40*     (2006.01)
*A61K 31/44*     (2006.01)
*C07D 401/00*    (2006.01)
*C07D 209/00*    (2006.01)

(52) U.S. Cl. ............... 514/339; 514/411; 514/416; 514/417; 546/142; 546/277.1; 548/210; 548/451; 548/472; 548/477

(58) Field of Classification Search ............... 514/339, 514/411, 416, 417; 546/142, 277.1; 548/210, 548/451, 472, 477
See application file for complete search history.

(56) References Cited

U.S. PATENT DOCUMENTS 7,034,052 B2 *   4/2006   Man et al. ............... 514/429

OTHER PUBLICATIONS

Borkakoti, Matrix Metalloproteases: Variations on a Theme, Progress in Biophysics & Molecular Biology, 1998, vol. 70, No. 1, pp. 73-94.*
Yu et al., Matrix Metalloproteases: Novel Targets for Directed Cancer Therapy, Drugs & Aging, Sep. 1997, vol. 11, No. 3, pp. 229-244.*

* cited by examiner

*Primary Examiner*—Brenda L Coleman
(74) *Attorney, Agent, or Firm*—Jones Day

(57) ABSTRACT

Imido and amido substituted acylhydroxamidic acids which reduce the levels of TNFα and inhibit phosphodiesterase in a mammal. A typical embodiment is (3-(1,3-dioxoisoindolin-2-yl)-3-(3-ethoxy-4-methoxyphenyl)propandylamino) propanoate.

6 Claims, No Drawings

SUBSTITUTED ACYLHYDROXAMIC ACIDS AND METHOD OF REDUCING TNFαLEVELS

This application is a division of application Ser. No. 09/468,529, filed Dec. 21, 1999, now U.S. Pat. No. 6,699,899 which is incorporated herein in its entirety.

FIELD OF THE INVENTION

The present invention relates to imido and amido substituted acylhydroxamic acids, the method of reducing levels or activities of cytokines such as tumor necrosis factor α in a mammal through the administration thereof, and pharmaceutical compositions of such derivatives.

BACKGROUND OF THE INVENTION

Tumor necrosis factor-α (TNFα) is a cytokine which is released primarily by cells of immune systems in response to certain immunostimulators. When administered to animals or humans, it causes inflammation, fever, cardiovascular effects, hemorrhage, coagulation, cachexia, and acute phase responses similar to those seen during acute infections, inflammatory diseases, and shock states. Excessive or unregulated TNFα production has been implicated in a number of disease conditions. These include endotoxemia and/or toxic shock syndrome [Tracey, et al., *Nature* 330, 662-664 (1987) and Hinshaw, et al., *Circ. Shock* 30, 279-292 (1990)], rheumatoid arthritis, inflammatory bowel disease, cachexia [Dezube, et al., *Lancet*, 335 (8690), 662 (1990)], and lupus. TNFα concentration in excess of 12,000 pg/mL have been detected in pulmonary aspirates from Adult Respiratory Distress Syndrome (ARDS) patients [Millar, et al., *Lancet* 2(8665), 712-714 (1989)]. Systemic infusion of recombinant TNFα resulted in changes typically seen in ARDS [Ferrai-Baliviera, et al., *Arch. Surg.* 124(12), 1400-1405 (1989)].

TNFα appears to be involved in a number of bone resorption diseases, including arthritis. When activated, leukocytes will produce bone-resorption. TNFα apparently contributes to this mechanism. [Bertolini, et al., *Nature* 319, 516-518 (1986) and Johnson, et al., *Endocrinology* 124(3), 1424-1427 (1989)]. TNFα also has been shown to stimulate bone resorption and inhibit bone formation in vitro and in vivo through stimulation of osteoclast formation and activation combined with inhibition of osteoblast functions. Another compelling link with disease is the association between production of TNFα by tumor or host tissues and malignancy associated hyper-calcemia [*Calci. Tissue Int. (US)* 46(Suppl.), S3-10 (1990)]. In Graft versus Host Reactions, increased serum TNFα levels have been associated with major complication following acute allogenic bone marrow transplants [Holler, et al., *Blood,* 75(4), 1011-1016 (1990)].

Validation of TNF-α inhibition as a clinical therapy has been demonstrated by the therapeutic use of TNF-α antibodies and soluble TNF-α receptors. TNFα blockage with monoclonal anti-TNFα antibodies has been shown to be beneficial in rheumatoid arthritis [Elliot, et al., *Int. J. Pharmac.* 1995 17(2), 141-145]. High levels of TNFα are associated with Crohn's disease [von Dullemen, et al., *Gastroenterology,* 1995 109(1), 129-135] treatment with soluble TNFα receptor treatment gave clinical benefits.

Cerebral malaria is a lethal hyperacute neurological syndrome associated with high blood levels of TNFα and the most severe complication occurring in malaria patients. Elevated levels of serum TNFα correlated directly with the severity of disease and the prognosis in patients with acute malaria attacks [Grau, et al., *N. Engl. J. Med.* 320(24), 1586-1591 (1989)].

TNFα plays a role in the area of chronic pulmonary inflammatory diseases. The deposition of silica particles leads to silicosis, a disease of progressive respiratory failure caused by a fibrotic reaction. Antibodies to TNFα completely blocked the silica-induced lung fibrosis in mice [Pignet, et al., *Nature,* 344, 245-247 (1990)]. High levels of TNFα production (in the serum and in isolated macrophages) have been demonstrated in animal models of silica and asbestos induced fibrosis [Bissonnette, et al., *Inflammation* 13(3), 329-339 (1989)]. Alveolar macrophages from pulmonary sarcoidosis patients have also been found to spontaneously release massive quantities of TNFα as compared with macrophages from normal donors [Baughman, et al., *J. Lab. Clin. Med.* 115(1), 36-42 (1990)].

Elevated levels of TNFα are implicated in reperfusion injury, the inflammatory response which follows reperfusion, and is a major cause of tissue damage after blood flow loss [Vedder, et al., *PNAS* 87, 2643-2646 (1990)]. TNFα also alters the properties of endothelial cells and has various pro-coagulant activities, such as producing an increase in tissue factor pro-coagulant activity, suppressing the anticoagulant protein C pathway, and down-regulating the expression of throm-bomodulin [Sherry, et al., *J. Cell Biol.* 107, 1269-1277 (1988)]. TNFα has pro-inflammatory activities which together with its early production (during the initial stage of an inflammatory event) make it a likely mediator of tissue injury in several important disorders including but not limited to, myocardial infarction, stroke and circulatory shock. TNFα-induced expression of adhesion molecules, such as intercellular adhesion molecules (ICAM) or endothelial leukocyte adhesion molecules (ELAM) on endothelial cells may be especially important [Munro, et al., *Am. J. Path.* 135(1), 121-132 (1989)].

It has been reported that TNFα is a potent activator of retrovirus replication including activation of HIV-1. [Duh, et al., *Proc. Nat. Acad. Sci.* 86, 5974-5978 (1989); Poll, et al., *Proc. Nat. Acad. Sci.* 87, 782-785 (1990); Monto, et al., *Blood* 79, 2670 (1990); Clouse, et al., *J. Immunol.* 142, 431-438 (1989); Poll, et al., *AIDS Res. Hum. Retrovirus,* 191-197 (1992)). At least three types or strains of HIV (i.e., HIV-1, HIV-2 and HIV-3) have been identified. As a consequence of HIV infection, T-cell mediated immunity is impaired and infected individuals manifest severe opportunistic infections and/or unusual neoplasms. HIV entry into the T-lymphocyte requires T-lymphocyte activation. Other viruses, such as HIV-1, HIV-2 infect T-lymphocytes after T-cell activation. This virus protein expression and/or replication is mediated or maintained by this T-cell activation. Once an activated T-lymphocyte is infected with HIV, the T-lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T-lymphocyte activation. Therefore, interference with cytokine activity such as prevention or inhibition of cytokine production, notably TNFα, in an HIV-infected individual assists in limiting the maintenance of T-lymphocyte caused by HIV infection.

Monocytes, macrophages, and related cells, such as kupffer and glial cells, also have been implicated in maintenance of the HIV infection. These cells, like T-cells, are targets for viral replication and the level of viral replication is dependent upon the activation state of the cells. (Rosenberg, et al., *The Immunopathogenesis of HIV Infection*, Advances in Immunology, 57 (1989)]. Cytokines, such as TNFα, have been shown to activate HIV replication in monocytes and/or macrophages [Poli, et al., *Proc. Natl. Acad. Sci.*, 87, 782-784 (1990)], therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells [Osborn, et al., *PNAS* 86 2336-2340]. This evidence suggests that a reduction of TNFα synthesis may have an antiviral effect in HIV infections, by reducing transcription and thus virus production.

AIDS viral replication of latent HIV in T cell and macrophage lines can be induced by TNFα [Folks, et al., *PNAS* 86, 2365-2368 (1989)]. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) [Osborn, et al., *PNAS* 86, 2336-2340 (1989)]. TNFα in AIDS associated cachexia is suggested by elevated serum TNFα and high levels of spontaneous TNFα production in peripheral blood monocytes from patients [Wright, et al., *J. Immunol.* 141(1), 99-104 (1988)]. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., *Cell* 1989, 58, 227-29). NFκB has been implicated as a transcriptional activator in a variety of disease and inflammatory states and is thought to regulate cytokine levels including but not limited to TNFα and active HIV transcription [Dbaibo, et al., *J. Biol. Chem.* 1993, 17762-66; Duh, et al., *Proc. Natl. Acad. Sci.* 1989, 86, 5974-78; Bachelerie, et al., *Nature* 1991, 350, 709-12; Boswas, et al., *J. Acquired Immune Deficiency Syndrome* 1993, 6, 778-786; Suzuki, et al., *Biochem. And Biophys. Res. Comm.* 1993, 193, 277-83; Suzuki, et al., *Biochem. And Biophys. Res Comm.* 1992, 189, 1709-15; Suzuki, et al., *Biochem. Mol. Bio. Int.* 1993, 31(4), 693-700; Shakhov, et al., *Proc. Natl. Acad. Sci. USA* 1990, 171, 35-47; and Staal, et al., *Proc. Natl. Acad. Sci. USA* 1990, 87, 9943-47]. Thus, it would be helpful to inhibit NFκB activation, nuclear translation or binding to regulate transcription of cytokine gene(s) and through this modulation and other mechanisms be useful to inhibit a multitude of disease states.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNFα and NFκB. Increased levels of cAMP also lead to the relaxation of airway smooth muscle.

The primary cellular mechanism for the inactivation of cAMP is the breakdown of cAMP by a family of isoenzymes referred to as cyclic nucleotide phosphodiesterases (PDE) [Beavo and Reitsnyder, *Trends in Pharm.*, 11, 150-155, 1990]. There are ten known members of the family of PDEs. It is well documented that the inhibition of PDE type IV (PDE 4) enzyme is particularly effective in both the inhibition of inflammatory mediator release and the relaxation of airway smooth muscle [Verghese, et al., *Journal of Pharmacology and Experimental Therapeutics*, 272(3), 1313-1320, 1995].

Decreasing TNFα levels and/or increasing cAMP levels thus constitutes a valuable therapeutic strategy for the treatment of many inflammatory, infectious, immunological, and malignant diseases. These include but are not restricted to: septic shock, sepsis, endotoxic shock, hemodynamic shock and sepsis syndrome, post ischemic reperfusion injury, malaria, mycobacterial infection, meningitis, psoriasis and other dermal diseases, congestive heart failure, fibrotic disease, cachexia, graft rejection, cancer, tumor growth, undesirable angiogenesis, autoimmune disease, opportunistic infections in AIDS, rheumatoid arthritis, rheumatoid spondylitis, osteoarthritis, other arthritic conditions, inflammatory bowel disease, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies [Beutler, et al., *Science* 234, 470-474 (1985); WO 92/11383].

Angiogenesis, the process of new blood vessel development and formation, plays an important role in numerous normal and pathological physiological events. Angiogenesis occurs in response to specific signals and involves a complex process characterized by infiltration of the basal lamina by vascular endothelial cells in response to angiogenic growth signal(s), migration of the endothelial cells toward the source of the signal(s), and subsequent proliferation and formation of the capillary tube. Blood flow through the newly formed capillary is initiated after the endothelial cells come into contact and connect with a preexisting capillary. Angiogenesis is required for tumor growth beyond a certain size.

Inhibitory influences predominate in the naturally occurring balance between endogenous stimulators and inhibitors of angiogenesis [Rastinejad, et al., 1989, *Cell* 56:345-355]. In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis [Moses, et al., 1991, *Biotech.* 9:630-634; Folkman, et al., 1995, *N. Engl. J. Med.*, 333:1757-1763; Auerbach, et al., 1985, *J. Microvasc. Res.* 29:401-411; Folkman, 1985, *Advances in Cancer Research*, eds. Klein and Weinhouse, Academic Press, New York, pp. 175-203; Patz, 1982, *Am. J. Opthalmol.* 94:715-743; and Folkman, et al., 1983, *Science* 221:719-725]. In a number of pathological conditions, the process of angiogenesis contributes to the disease state. For example, significant data suggests that the growth of solid tumors is dependent on angiogenesis [Folkman and Klagsbrun, 1987, *Science* 235:442-447].

The maintenance of the avascularity of the cornea, lens, and trabecular meshwork is crucial for vision as well as for ocular physiology. See, e.g., reviews by Waltman, et al., 1978, *Am. J. Ophthal.* 85:704-710 and Gartner, et al., 1978, *Surv. Ophthal.* 22:291-312. Currently, the treatment of these diseases, especially once neovascularization has occurred, is inadequate and blindness often results.

An inhibitor of angiogenesis could have an important therapeutic role in limiting the contributions of this process to pathological progression of the underlying disease states as well as providing a valuable means of studying their etiology. For example, agents that inhibit tumor neovascularization could play an important role in inhibiting metastatic and solid tumor growth.

Several kinds of compounds have been used to prevent angiogenesis. Taylor, et al. used protamine to inhibit angiogenesis, [Taylor, et al., Nature 297:307 (1982)]. The toxicity of protamine limits its practical use as a therapeutic. Folkman, et al. used heparin and steroids to control angiogenesis. [Folkman, et al., Science 221:719 (1983) and U.S. Pat. Nos. 5,001,116 and 4,994,443]. Steroids, such as tetrahydrocortisol, which lack gluco and mineral corticoid activity, are angiogenic inhibitors. Interferon β is also a potent inhibitor of angiogenesis induced by allogeneic spleen cells [Sidky, et al., Cancer Research 47:5155-5161 (1987)]. Human recombinant interferon-α was reported to be successfully used in the treatment of pulmonary hemangiomatosis, an angiogenesis-induced disease [White, et al., New England J. Med. 320:1197-1200 (1989)].

Other agents which have been used to inhibit angiogenesis include ascorbic acid ethers and related compounds [Japanese Kokai Tokkyo Koho No. 58-131978]. Sulfated polysaccharide DS 4152 also shows angiogenic inhibition [Japanese Kokai Tokkyo Koho No. 63-119500]. A fungal product, fumagillin, is a potent angiostatic agent in vitro. The compound is toxic in vivo, but a synthetic derivative, AGM 12470, has been used in vivo to treat collagen II arthritis. Fumagillin and o-substituted fumagillin derivatives are disclosed in EPO Publication Nos. 0325199A2 and 0357061A1.

In U.S. Pat. No. 5,874,081, Parish teaches use of monoclonal antibodies to inhibit angiogenesis. In WO92/12717, Brem, et al. teach that some tetracyclines, particularly Minocycline, Chlortetracycline, Demeclocycline and Lymecycline are useful as inhibitors of angiogenesis. Brem, et al. teach that Minocycline inhibits angiogenesis to an extent comparable to that of the combination therapy of heparin and cortisone [*Cancer Research,* 51, 672-675, Jan. 15, 1991]. Teicher, et al. teach that tumor growth is decreased and the number of metastases is reduced when the anti-angiogenic agent of metastases is reduced when the anti-angiogenic agent Minocycline is used in conjunction with cancer chemotherapy or radiation therapy [*Cancer Research,* 52, 6702-6704, Dec. 1, 1992].

Macrophage-induced angiogenesis is known to be stimulated by TNFα. Leibovich, et al. reported that TNFα induces in vivo capillary blood vessel formation in the rat cornea and the developing chick chorioallantoic membranes at very low doses and suggested TNFα is a candidate for inducing angiogenesis in inflammation, wound repair, and tumor growth [*Nature,* 329, 630-632 (1987)].

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, brain cancer, melanoma, lymphoma, erythroleukemia, uterine cancer, bone cancer, and head and neck cancer.

Cancer is now primarily treated with one or a combination of three types of therapies: surgery, radiation, and chemotherapy. Surgery involves the bulk removal of diseased tissue. While surgery is sometimes effective in removing tumors located at certain sites (e.g., in the breast, colon, and skin) surgery cannot be used in the treatment of tumors located in other areas (e.g., the backbone) nor in the treatment of disseminated neoplastic conditions (e.g., leukemia). Chemotherapy involves the disruption of cell replication or cell metabolism. Chemotherapy is used most often in the treatment of leukemia, as well as breast, lung, and testicular cancer.

Chemotherapeutic agents are often referred to as antineoplastic agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastrointestinal mucosa, and fetal tissue. Antimetabolites are typically reversible or irreversible enzyme inhibitors, or compounds that otherwise interfere with the replication, translation or transcription of nucleic acids. Thus, it would be preferable to find less toxic compounds for cancer treatment.

Matrix metalloproteinase (MMP) inhibition has been associated with several activities including inhibition of TNFα [Mohler, et al., *Nature,* 370, 218-220 (1994)] and inhibition of angiogenesis. MMPs are a family of secreted and membrane-bound zinc endopeptidases that play a key role in both physiological and pathological tissue degradation [Yu, et al., *Drugs & Aging,* 1997, (3):229-244; Wojtowicz-Praga, et al., *Int. New Drugs,* 16:61-75 (1997)]. These enzymes are capable of degrading the components of the extracellular matrix, including fibrillar and non-fibrillar collagens, fibronectin, laminin, and membrane glycoproteins. Ordinarily, there is a delicate balance between cell division, matrix synthesis, matrix degradation (under the control of cytokines), growth factors, and cell matrix interactions. Under pathological conditions, however, this balance can be disrupted. Conditions and diseases associated with undesired MMP levels include, but are not limited to: tumor metastasis invasion and growth, angiogenesis, rheumatoid arthritis, osteoarthritis, osteopenias such as osteoporosis, periodontitis, gingivitis, Crohn's disease, inflammatory bowel disease, and corneal epidermal or gastric ulceration.

Increased MMP activity has been detected in a wide range of cancers [Denis, et al., *Invest. New Drugs,* 15: 175-185 (1987)]. As with TNFα, MMPs are believed to be involved in the invasive processes of angiogenesis and tumor metastasis.

DETAILED DESCRIPTION

The present invention is based on the discovery that certain classes of compounds more fully described herein decrease the levels of TNFα, increase cAMP levels, inhibit phosphodiesterases (PDEs, in particular PDE 4), affect tumors, and affect angiogenesis.

The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, sepsis, endotoxic shock, graft versus host disease, wasting, inflammatory bowel disease, Crohn's disease, ulcerative colitis, multiple sclerosis, systemic lupus erythrematosis, ENL in leprosy, cancer, HIV, AIDS, and opportunistic infections in AIDS. TNFα and NFκB levels are influenced by a reciprocal feedback loop. As noted above, the compounds of the present invention affect the levels of both TNFα and NFκB. Compounds in this application inhibit PDE4.

In particular, the invention pertains to (a) compounds of the formula:

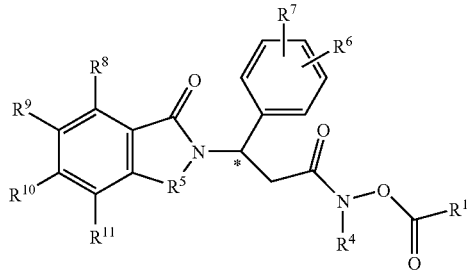

Formula I wherein the carbon atom designated * constitutes a center of chirality, $R^4$ is hydrogen or —(C=O)—$R^{12}$;

each of $R^1$ and $R^{12}$, independently of each other, is alkyl of 1 to 6 carbon atoms, phenyl, benzyl, pyridyl methyl, pyridyl, imidazoyl, imidazolyl methyl, or CHR*(CH$_2$)$_n$NR*R$^0$ wherein R* and R$^0$, independently of the other, are hydrogen, alkyl of 1 to 6 carbon atoms, phenyl, benzyl, pyridylmethyl, pyridyl, imidazoyl or imidazolylmethlyl, and n=0, 1, 2;

$R^5$ is C=O, CH$_2$, CH$_2$—CO—, or SO$_2$;

each of $R^6$ and $R^7$, independently of the other, is nitro, cyano, trifluoromethyl, carbethoxy, carbomethoxy, carbopropoxy, acetyl, carbamoyl, acetoxy, carboxy, hydroxy, amino, alkyl of 1 to 6 carbon atoms, alkoxy of 1 to 6 carbon atoms, cycloalkoxy of 3 to 8 carbon atoms, halo, bicycloalkyl of up to 18 carbon atoms, tricycloalkoxy of up to 18 carbon atoms, 1-indanyloxy, 2-indanyloxy, C$_4$-C$_8$-cycloalkylidenemethyl, or C$_3$-C$_{10}$-alkylidenemethyl;

each of $R^8$, $R^9$, $R^{10}$, and $R^{11}$, independently of the others, is (i) hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, halo, or (ii) one of $R^8$, $R^9$, $R^{10}$, and $R^{11}$ is acylamino comprising a lower alkyl, and the remaining of $R^8$, $R^9$, $R^{10}$, and $R^{11}$ are hydrogen, or (iii) hydrogen if $R^8$ and $R^9$ taken together are benzo, quinoline, quinoxaline, benzimidazole, benzodioxole, 2-hydroxybenzimidazole, methylenedioxy, dialkoxy, or dialkyl, or (iv) hydrogen if $R^{10}$ and $R^{11}$, taken together are benzo, quinoline, quinoxaline, benzimidazole, benzodioxole, 2-hydroxybenzimidazole, methylenedioxy, dialkoxy, or dialkyl, or (v) hydrogen if $R^9$ and $R^{10}$ taken together are benzo; and (b) The acid addition salts of said compounds which contain a nitrogen atom capable of being protonated.

The invention also relates to a compound of the formula:

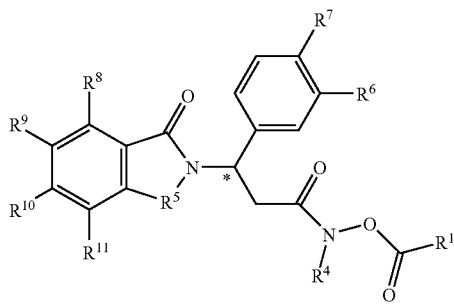

in which the carbon atom designated * constitutes a center of chirality;

$R^4$ is hydrogen or —(C=O)—$R^{12}$, where each of $R^1$ and $R^{12}$, independently of each other, is alkyl of 1 to 6 carbon atoms, phenyl, benzyl, pyridyl, pyridyl methyl, imidazolyl, imidazoylmethyl, or CHR*(CH$_2$)$_n$NR*R$^0$ wherein R* and R$^0$, independently of the other, are hydrogen, alkyl of 1 to 6 carbon atoms, phenyl, benzyl, pyridylmethyl, pyridyl, imidazoyl or imidazolylmethyl, and n=0, 1, 2;

$R^5$ is C=O or CH$_2$;

each of $R^6$ and $R^7$, independently of the other is alkoxy of 1 to 8 carbon atoms, cycloalkoxy of 3 to 6 carbon atoms; C$_4$-C$_6$-cycloalkylidenemethyl, C$_2$-C$_{10}$-alkylidenemethyl, C$_6$-C$_{18}$-bicycloalkoxy, C$_6$-C$_{18}$-tricycloalkoxy, 1-indanyloxy, or 2-indanyloxy; and each of $R^8$, $R^9$, $R^{10}$, and $R^{11}$, independently of the others, is hydrogen, nitro, cyano, trifluoromethyl, carbethoxy, carbomethoxy, carbopropoxy, acetyl, halo, carbamoyl, acetoxy, carboxy, hydroxy, amino, alkylamino, dialkylamino, acylamino, alkyl of 1 to 10 carbon atoms, and alkoxy of 1 to 10 carbon atoms.

The carbon atom designated with an * constitutes a center of chirality. Both optical isomers are part of this invention. Unless otherwise defined, the preferred R group of R—(C=O)— in acyl and the acyl of acylamino in this invention is alkyl of 1 to 6 carbon atoms, phenyl, benzyl, pyridylmethyl, pyridyl, imidazoyl, imidazolylmethlyl, or CHR*(CH$_2$)$_n$NR*R$^0$, wherein R*and R$^0$, independently of the other, are hydrogen, alkyl of 1 to 6 carbon atoms, phenyl, benzyl, pyridylmethyl, pyridyl, imidazoyl or imidazolylmethlyl, and n=0, 1, 2. Alkyl is preferably unbranched. Branched and/or cyclic alkyl forms are also envisioned.

Subgroups of Formula I can include the following: The acylhydroxamic acid derivative in Formula I, wherein $R^4$ is hydrogen; $R^5$ is C=O; $R^8$ is hydrogen; and one of $R^9$ and $R^{11}$ is hydrogen and the other of $R^9$ and $R^{11}$, taken together with $R^{10}$, is benzo, methylenedioxy, dioxo, or dialkoxy. The acylhydroxamic acid derivative in Formula I, wherein $R^4$ is hydrogen; $R^5$ is C=O; $R^8$ and $R^9$ are hydrogen; and $R^{10}$ and $R^{11}$, taken together, are methylenedioxy. The acylhydroxamic acid derivative in Formula I, wherein one or more of $R^8$, $R^9$, $R^{10}$, and $R^{11}$, independently of the others, is hydrogen, alkyl of 1 to 10 carbon atoms, or alkoxy of 1 to 10 carbon atoms. The acylhydroxamic acid derivative in Formula I, wherein $R^8$, $R^9$, $R^{10}$, and $R^{11}$ are (a) at least one alkyl of 1 to 10 carbon atoms (i.e., a lower alkyl) with the remainder of $R^8$, $R^9$, $R^{10}$, and $R^{11}$ being hydrogen, or (b) at least one alkoxy of 1 to 10 carbon atoms with the remainder of $R^8$, $R^9$, $R^{10}$, and $R^{11}$ being hydrogen. For the purposes of this invention, acylamino includes acetamido. The acylhydroxyamic acid derivative in Formula I, which is a substantially chirally pure (3R)-isomer, a substantially chirally pure (3S)-isomer, or a mixture thereof. The acylhydroxamic acid derivative in Formula I, wherein $R^4$ is hydrogen. The acylhydroxamic acid derivative in Formula I, wherein $R^4$ is —(C=O)—$R^{12}$. The acylhydroxamic acid derivative in Formula I, wherein each of $R^8$, $R^9$, $R^{10}$, and $R^{11}$ is hydrogen, halo, alkyl of 1 to 4 carbon atoms, or alkoxy of 1 to 4 carbon atoms. The acylhydroxamic acid derivative in Formula I, wherein one of $R^8$, $R^9$, $R^{10}$, or $R^{11}$ is amino, acylamino, alkylamino, dialkylamino, or hydroxy. An acylhydroxamic acid derivative in Formula I, wherein $R^1$ is alkyl of 1 to 10 carbon atoms, pyridyl, or imidazolyl.

Unless otherwise defined, the term alkyl denotes a univalent saturated branched or straight hydrocarbon chain containing from 1 to 10 carbon atoms. Representative of such alkyl groups are methyl, ethyl, propyl, isopropyl, butyl, isobutyl, sec-butyl, and tert-butyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, and tert-butoxy. Acetylamino also includes the name acetamido. Methylenedioxy may sometimes be called dioxo.

In Formula I, each of $R^8$, $R^9$, $R^{10}$, and $R^{11}$ can be hydrogen, halo, alkyl of 1 to 4 carbon atoms, or alkoxy of 1 to 4 carbon atoms. Alternatively, one of $R^8$, $R^9$, $R^{10}$, and $R^{11}$ is amino, alkyl amino, dialkyl amino, or acyl amino, alkyl of 1 to 10 carbon atoms, alkoxy of 1 to 10 carbon atoms, or hydroxy, and the remaining of $R^8$, $R^9$, $R^{10}$, and $R^{11}$ are hydrogen. Formula I, can also have $R^8$, $R^9$, $R^{10}$, and $R^{11}$ as hydrogen. Formula I can be a substantially chirally pure (R)-isomer, a substantially chirally pure (S)-isomer, or a mixture thereof.

A pharmaceutical composition can contain a quantity of an acylhydroxamic acid derivative of Formula I, which derivative is a substantially chirally pure (R)-isomer, a substantially chirally pure (S)-isomer, or a mixture thereof, sufficient upon administration in a single or multiple dose regimen to reduce or inhibit levels of TNFα or to treat cancer, undesired angiogenesis, or arthritis in a mammal in combination with a carrier. A pharmaceutical composition can contain a quantity of Formula I which is a substantially chirally pure (R)-isomer, a substantially chirally pure (S)-isomer, or a mixture thereof, sufficient upon administration in a single or multiple dose regimen to inhibit undesirable levels of matrix metalloproteinases and/or PDE4 in a mammal in combination with a carrier.

This invention includes the following methods along with other reasonably expected methods. A method of reducing or inhibiting undesirable levels of TNFα in a mammal which comprises administering thereto an effective amount of an acylhydroxamic acid derivative of Formula I, which derivative is a substantially chirally pure (R)-isomer, a substantially chirally pure (S)-isomer, or a mixture thereof. A method of reducing or inhibiting undesirable levels of matrix metalloproteinases in a mammal which comprises administering thereto an effective amount of an acylhydroxamic acid derivative of Formula I, which derivative is a substantially chirally pure (R)-isomer, a substantially chirally pure (S)-isomer, or a mixture thereof. A method of treating in a mammal a disease selected from the group consisting of but not limited to inflammatory disease, autoimmune disease, arthritis, rheumatoid arthritis, inflammatory bowel disease, Crohn's disease, aphthous ulcers, cachexia, graft versus host disease, asthma, adult respiratory distress syndrome, and acquired immune deficiency syndrome, which comprises administering thereto an effective amount of a compound described by Formula I, which compound is a substantially chirally pure (R)-isomer, a substantially chirally pure (S)-isomer, or a mixture thereof. A method of treating cancer in a mammal which comprises administering thereto an effective amount of a compound described by Formula I, which compound is a substantially chirally pure (R)-isomer, a substantially chirally pure (S)-isomer, or a mixture thereof. A method of treating undesirable angiogenesis in a mammal which comprises administering thereto an effective amount of a compound described by Formula I, which compound is a substantially chirally pure (R)-isomer, a substantially chirally pure (S)-isomer, or a mixture thereof. Also included in this invention is a method of reducing or inhibiting phosphodiesterases IV (PDE4) in a mammal which comprises administering thereto an effective amount of an acylhydroxamic acid derivative described by Formula I, which derivative is a substantially chirally pure (R)-isomer, a substantially chirally pure (R)-isomer, or a mixture thereof.

The compounds of Formula I are used, under the supervision of qualified professionals, to inhibit the undesirable effects of TNFα and/or inhibit phosphodiesterases, and/or inhibit inflammation and/or angiogenesis and/or cancer. Inhibition of the phosphodiesterase type 4 (PDE4 or PDE IV) is the preferred embodiment in this application. The compounds can be administered orally, rectally, or parenterally, alone or in combination with other therapeutic agents including antibiotics, steroids, etc., to a mammal in need of treatment.

The compounds of the present invention also can be used topically in the treatment or prophylaxis of topical disease states mediated or exacerbated by inflammation excessive TNFα production, excessive MMPs, or where increased cAMP levels will be helpful, Some examples include viral infections, such as those caused by the herpes viruses or viral conjunctivitis, or dermal conditions such as psoriasis or atopic dermatitis, etc.

The compounds can also be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Angiogenesis, the process of new blood vessel development and formation, plays an important role in numerous physiological events, both normal and pathological. The compounds also can be used to inhibit unwanted angiogenesis. The compounds may also be used to inhibit tumor growth.

The invention also relates to MMP-inhibiting compounds, compositions thereof, and their use in the treatment of diseases and disorders associated with undesired production or activity of MMPs. These compounds are capable of inhibiting connective tissue breakdown, and are useful in the treatment or prevention of conditions involving tissue breakdown. These include, but are not limited to, tumor metastasis, invasion, and growth, rheumatoid arthritis, osteoarthritis, osteopenias such as osteoporosis, periodontitis, gingivitis, and corneal epidermal inflammatory bowel disease, or gastric ulceration.

The following Formulas are related as follows. The compounds according to Formula III are the starting material for the compounds of Formula II. The compound of Formula II is the starting material for the compounds of Formula IV in Reaction a to produce the compound of Formula I(b).

The compounds of Formula IV are readily prepared by reacting a carboxylic acid of the formula:

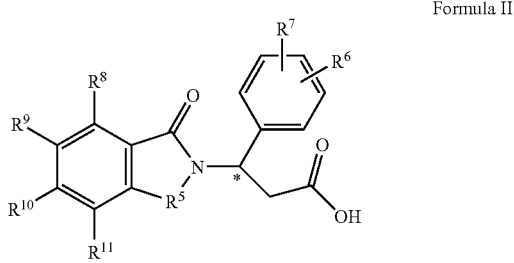

Formula II with hydroxylamine hydrochloride or an alkoxyamine hydrochloride in the presence of a coupling agent. $R^5$, $R^6$, $R^7$, $R^8$, $R^9$, $R^{10}$, and $R^{11}$ are defined above. The reaction generally is conducted in an inert solvent such as tetrahydrofuran, ethyl acetate, etc. under an inert atmosphere such as nitrogen. Ambient or above ambient temperatures can be employed. When the reaction is substantially complete, generally the products can be readily isolated simply through the addition of water.

The compounds of Formula II which are here utilized as intermediates are described in U.S. Pat. No. 5,605,914, the disclosure of which is incorporated herein by reference. Briefly, such intermediates can be prepared through the reaction of an amino acid of the formula:

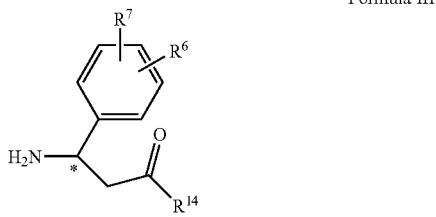

Formula III in which $R^{14}$ is hydroxy, alkoxy, or a protecting group, with an anhydride, an N-carbethoxyimide, a dialdehyde, or an o-bromo aromatic acid.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol. 15/I, Georg Thieme Verlag, Stuttgart 1974, the disclosures of which are incorporated herein by reference.

In any of the foregoing reactions, a nitro compound can be employed with the nitro group being converted to an amino group by catalytic hydrogenation or chemical reaction. Alternatively, a protected amino group can be deprotected to yield the corresponding amino compound. An amino group can be protected as an amide utilizing an acyl group which is selectively removable under mild conditions, especially benzyloxycarbonyl, formyl, or a lower alkanoyl group, each of which is branched in a 1- or α position to the carbonyl group, particularly tertiary alkanoyl such as pivaloyl, a lower alkanoyl group which is substituted in the position α to the carbonyl group, as for example trifluoroacetyl.

In a preferred embodiment, hydroxamic acids such as those prepared above can be reacted with acid anhydrides, in acetonitrile ($CH_3CN$) or other inert solvent as follows:

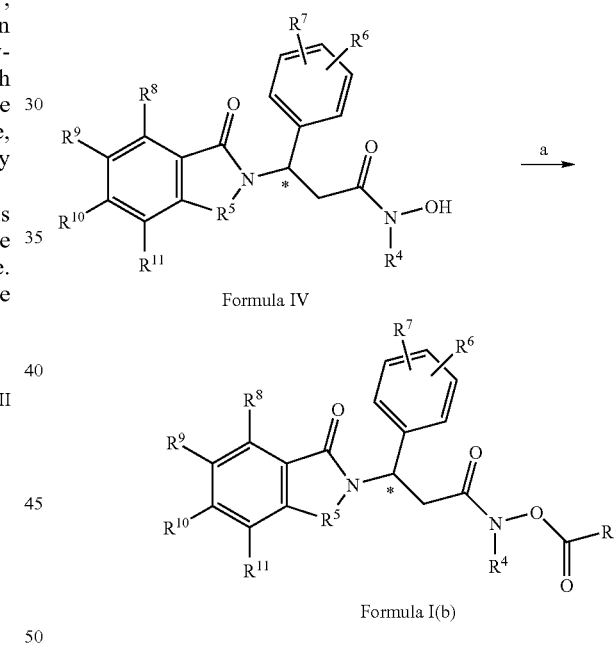

in which Reaction a is a reaction of IV with an anhydride of the formula $(R^1CO)_2O$ in $CH_3CN$. $R^1$, $R^4$, $R^5$, and $R^6$ to $R^{11}$ are defined above. A mixture of two main reaction products (A) and (B) may result. The first reaction product (A) has $R^4$ being hydrogen. The second reaction product (B) has $R^4$ being —(C=O)—$R^{12}$. $R^{12}$ is defined above. Reaction products (A) and (B) can be purified by column chromatography. The crude product can also be slurried in hexane several times to afford pure reaction product (A). Reaction product (B), where $R^{12}$ is not the same as $R^1$, can be prepared from treatment of (A) with an acid anhydride containing the desired $R^{12}$ group. Formula I(b) is Formula I or can be a subgroup of Formula I.

The compounds of Formula I possess at least one center of chirality (designated by "*") and thus can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid or base, such as the individual enantiomers of 10-camphorsulfonic acid, camphoric acid, α-bromocamphoric acid, methoxyacetic acid, tartaric acid, di-acetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%. Chiral bases can also be used for this process.

Formula I(c) is a subgroup of Formula I. Formula 1(c) represents (a) an acylhydroxamic acid derivative having the formula:

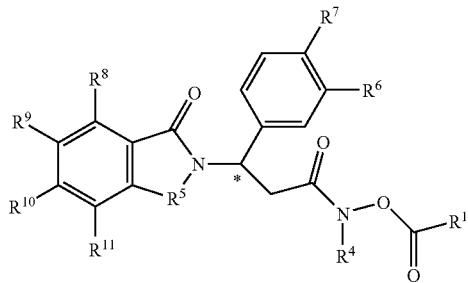

Formula 1(c)

in which
the carbon atom designated * constitutes a center of chirality,
$R^4$ is hydrogen or —(C=O)—$R^{12}$;
each of $R^1$ and $R^{12}$, independently of each other, is alkyl of 1 to 6 carbon atoms, phenyl, benzyl, pyridyl methyl, pyridyl, imidazoyl, imidazolyl methyl, or CHR*(CH$_2$)$_n$NR*R$^0$;
wherein R* and $R^0$, independently of the other, are hydrogen, alkyl of 1 to 6 carbon atoms, phenyl, benzyl, pyridylmethyl, pyridyl, imidazoyl or imidazolylmethlyl, and n=0, 1, 2;
$R^5$ is C=O, CH$_2$, CH$_2$—CO—, or SO$_2$;
each of $R^6$ and $R^7$, independently of the other, is nitro, cyano, trifluoromethyl, carbethoxy, carbomethoxy, carbopropoxy, acetyl, carbamoyl, acetoxy, carboxy, hydroxy, amino, alkyl of 1 to 6 carbon atoms, alkoxy of 1 to 8 carbon atoms, cycloalkoxy of 3 to 8 carbon atoms, halo, bicycloalkyl of up to 18 carbon atoms, tricycloalkoxy of up to 18 carbon atoms, 1-indanyloxy, 2-indanyloxy, $C_4$-$C_8$-cycloalkylidenemethyl, or $C_2$-$C_{10}$-alkylidehemethyl;
each of $R^8$, $R^9$, $R^{10}$, and $R^{11}$, independently of the others, is
(i) hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, halo, or
(ii) one of $R^8$, $R^9$, $R^{10}$, and $R^{11}$ is acylamino comprising a lower alkyl, and the remaining of $R^8$, $R^9$, $R^{10}$, and $R^{11}$ are hydrogen, or (iii) hydrogen if $R^8$ and $R^9$ taken together are benzo, quinoline, quinoxaline, benzimidazole, benzodioxole, 2-hydroxybenzimidazole, methylenedioxy, dialkoxy, or dialkyl, or
(iv) hydrogen if $R^{10}$ and $R^{11}$, taken together are benzo, quinoline, quinoxaline, benzimidazole, benzodioxole, 2-hydroxybenzimidazole, methylenedioxy, dialkoxy, or dialkyl, or
(v) hydrogen if $R^9$ and $R^{10}$ taken together are benzo; and
(b) The acid addition salts of said compounds which contain a nitrogen atom capable of being protonated.

The present invention also pertains to the physiologically acceptable non-toxic acid addition salts of the compound of Formula I. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formulas I or the compounds of the product in Reaction a associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, polyvinylpyrrolidone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermine fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

TNFα inhibition in LPS stimulated human peripheral blood mononuclear cells (PBMCs) can be performed as described below. Enzyme-linked immunosorbent assays (ELISA) for TNFα can be performed in a conventional manner. PBMCs are isolated from normal donors by Ficoll-Hypaque density centrifugation. Cells are cultured in RPMI supplemented with 10% AB+ serum, 2 mM L-glutamine, 100 U/mL (units per milliliter) penicillin, and 100 mg/mL streptomycin. Drugs are dissolved in dimethylsulfoxide (Sigma Chemical) and further dilutions are done in supplemented RPMI (a well known media). The final dimethylsulfoxide concentration in the presence or absence of drug in the PBMC suspensions is 0.25 wt %. Drugs are assayed at half-log or log dilutions starting at 100 µM. Drugs are added to PBMC ($10^6$ cells/mL) in 96 wells plates one hour before the addition of LPS. PBMCs ($10^6$ cells/mL) in the presence or absence of drug are stimulated by treatment with 1 µg/mL or 100 ng/mL of LPS from *Salmonella minnesota* R595 (List Biological Labs, Campbell, Calif.). Cells are then incubated at 37° C. for 18-20 hours. Supernatants are harvested and assayed immediately for TNFα levels or kept frozen at 31 70° C. (for not more than 4 days) until assayed. The concentration of TNFα in the supernatant is determined by human TNFα ELISA kits (ENDOGEN, Boston, Mass.) according to the manufacturer's directions.

Inhibition of phosphodiesterase type 4 (PDE 4) can also be determined in conventional models. For example, using a modification of the method of Hill and Mitchell, U937 cells (a human promonocytic cell line) are grown to $1\times10^6$ cells/mL and collected by centrifugation. A cell pellet of $1\times10^9$ cells is washed in phosphate buffered saline and then frozen at −70° C. for later purification or immediately lysed in cold homogenization buffer (20 mM Tris-HCl, pH 7.1, 3 mM 2-mercaptoethanol, 1 mM magnesium chloride, 0.1 mM ethylene glycol-bis-(β-aminoethyl ether)-N,N,N',N'-tetraacetic acid (EGTA), 1 µM phenylmethylsulfonyl fluoride (PMSF), and 1 µg/mL leupeptin). Cells are homogenized with 20 strokes in a Dounce homogenizer and the supernatant containing the cytosolic fraction are obtained by centrifugation. The supernatant is then loaded onto a Sephacryl. S-200 column equilibrated in homogenization buffer. The crude phosphodiesterase type 4 enzyme is eluted in homogenization buffer at a rate of approximately 0.5 mL/min and fractions are assayed for phosphodiesterase activity using rolipram. Fractions containing PDE 4 activity (rolipram sensitive) are pooled and aliquoted for later use.

The phosphodiesterase assay is carried out based on the procedure described by Hill and Mitchell [Hill and Mitchell, *Faseb J.*, 8, A217 (1994)]. The assay is carried out in a total volume of 100 µl containing various concentration of the compounds of interest, 50 mM Tris-HCl, pH 7.5, 5 mM magnesium chloride and 1 µM cAMP of which 1% is $^3$H cAMP. Reactions are incubated at 30° C. for 30 minutes and then terminated by boiling for 2 minutes. The amount of PDE 4 containing extract used for these experiments is predetermined such that reactions are within the linear range and consume less than 15% of the total substrate. Following termination of reaction, samples are chilled at 4° C. and then treated with 10 µL of 10 mg/mL snake venom for 15 min at 30° C. Unused substrate then is removed by adding 200 µl of a quaternary ammonium ion exchange resin (AG1-X8, BioRad) for 15 minutes. Samples then are spun at 3000 rpm, 5 min and 50 µl of the aqueous phase are taken for counting. Each data point is carried out in duplicate and activity is expressed as percentage of control. The $IC_{50}$s of the compounds are then determined from dose response curves of a minimum of three independent experiments.

Representative examples include a substantially chirally pure (R)-isomer, a substantially, chirally pure (S)-isomer, or a mixture thereof, where the isomer is (3-(1, 3-dioxoisoindolin-2-yl)-3-(3-ethoxy-4-methoxyphenyl)propanoylamino) propanoate; (3-(1,3-dioxoisoindolin-2-yl)-3-(3-ethoxy-4-methoxyphenyl)propanoylamino)acetate; (3-(1,3-dioxoisoindolin-2-yl)-3-(3-ethoxy-4-methoxyphenyl) propanoylamino)-pentanoate; (3-(1,3-dioxoisoindolin-2-yl)-3-(3-ethoxy-4-methoxyphenyl)propanoyl-amino)benzoate; (3-(3-cyclopentyloxy-4-methoxy phenyl)-3-(1-oxoisoindolin-2-yl)propanoylamino)acetate; (3-[4-(acetylamino)-1,3-dioxoisoindolin-2-yl]-3-(3-ethoxy-4-methoxyphenyl)propanoylamino)acetate; (3-(3-ethoxy-4-methoxyphenyl)-3-(4-methyl-1,3-dioxoisoindolin-2-yl)propanoyl amino)acetate; (3-(3-ethoxy-4-methoxy-phenyl)-3-(5-methyl-1,3-dioxoisoindolin-2-yl)propanoylamino)acetate; (3-(3-cyclo-pentyloxy-4-methoxyphenyl)-3-(4-methyl-1,3-dioxoisoindolin-2-yl)propanoylamino)acetate; (3-(3-cyclopentyloxy-4-methoxyphenyl)-3-(5-methyl-1,3-dioxoisoindolin-2-yl) propanoylamino)acetate; -N-acetyl-3-(3-ethoxy-4-methoxyphenyl)-3-(5-methyl-1,3-dioxoisoindolin-2-yl) propanoylamino)acetate; N-acetyl-3-(3-cyclopentyloxy-4-methoxy-phenyl)-3-(4-methyl-1,3-dioxoisoindolin-2-yl) propanoylamino)acetate; (3-[5-(acetylamino)-1,3-dioxoisoindolin-2-yl]-3-(3-ethoxy-4-ethoxyphenyl) propanoylamino)acetate; (3-(1,3-dioxobenzo[e] isoindolin-2-yl)-3-(3-ethoxy-4-methoxyphenyl)propanoyl-amino) acetate; (3-(3-ethoxy-4-methoxyphenyl)-3-phthalimido-propanoyl-amino)pyridine-3-carboxylate; (3-[4-(acetylamino)-1,3-dioxoisoindolin-2-yl]-3-(3-cyclopentyloxy-4-methoxyphenyl)propanoylamino)acetate; (N-acetyl-3-[4-(acetyl-amino)-1,3-dioxoisoindolin-2-yl]-3-(3-cyclopentyloxy-4-methoxyphenyl)propanoyl-amino)acetate; or (3-(3-ethoxy-4-methoxyphenyl)-3-(1-oxoisoindolin-2-yl)propanoyl-amino)acetate. The following examples will serve to further typify the nature of this invention but should not be construed as a limitation in the scope thereof, which scope is defined solely by the appended claims.

EXAMPLE 1

(3-(1,3-Dioxoisoindolin-2-yl)-3-(3-ethoxy-4-methoxyphenyl)propanoylamino)propanoate A mixture of 3-(1,3-dioxoisoindolin-2-yl)-3-(3-ethoxy-4-methoxyphenyl)propanehydroxamic acid (5.8 g, 15 mmol) and propionic anhydride (3.93 g, 30.2 mmol) in anhydrous acetonitrile (170 mL) was stirred at room temperature under nitrogen overnight. Removal of solvent in vacuo yielded an oil. The oil was then stirred in ether (25 mL). The resulting suspension was filtered and washed with ether to give (3-(1,3-dioxoisoindolin-2-yl)-3-(3-ethoxy-4-methoxyphenyl)propanoylamino)propanoate as a white solid (2.8 g, 42%): mp, 181.0-183.5° C.; $^1$H NMR (DMSO-d6) δ 1.01 (t, J=7.5 Hz, 3H, $CH_2CH_3$), 1.31 (t, J=6.9 Hz, 3H, $OCH_2CH_3$), 2.39 (q, J=7.4 Hz, 2H, $CH_2$), 3.12-3.35 (m, 2H, $CH_2$), 3.97 (q, J=7.4 Hz, 2H, $CH_2$), 5.67 (t, J=7.7 Hz, 1H, CH), 6.90 (s, 2H, Ar), 7.02 (s, 1H, Ar), 7.83-7.86 (m, 4H, Ar), 11.87 (br, s, 1H, NH); $^{13}$C NMR (DMSO-d6) δ 8.2, 14.1, 23.7, 33.4, 49.3, 54.9, 63.2, 111.3, 111.7, 118.9, 122.6, 130.5, 130.7, 134.6, 147.2, 148.1, 166.1, 167.1, 171.1; Anal. Calcd. For $C_{23}H_{24}N_2O_7$: C, 62.72; H, 5.49; N, 6.36. Found: C, 62.62; H, 5.50; N, 6.18.

EXAMPLE 2

(3-(1,3-Dioxoisoindolin-2-yl)-3-(3-ethoxy-4-methoxyphenyl)propanoylamino)acetate (3-(1,3-Dioxoisoindolin-2-yl)-3-(3-ethoxy-4-methoxyphenyl)propanoylamino)acetate was prepared by the procedure of Example 1 from 3-(1,3-dioxoisoindolin-2-yl)-3-(3-ethoxy-4-methoxyphenyl)propanehydroxamic acid (0.5 g, 1.3 mmol) and acetic anhydride (0.27 g, 2.6 mmol) in anhydrous acetonitrile (20 mL). The product was obtained as a white solid (0.25 g, 45%): mp, 180.0-182.0° C.; $^1$H NMR (DMSO-d6) δ 1.31 (t, J=6.7 Hz, 3H, CH$_3$), 2.07 (s, 3H, CH$_3$), 3.10-3.26 (m, 2H, CH$_2$), 3.72 (s, 3H, OCH$_3$), 4.00 (q, J=6.4 Hz, 2H, OCH$_2$), 5.67 (t, J=7.7 Hz, 1H CH), 6.89 (s, 2H, Ar), 7.02 (s, 1H, Ar), 7.82-7.85 (m, 4H, Ar), 11.86 (br s, 1H, NH); $^{13}$C NMR (DMSO-d6) δ 14.6, 17.9, 33.9, 49.8, 55.4, 63.7, 111.8, 112.1, 119.4, 123.1, 130.9, 131.2, 134.5, 147.7, 148.5, 166.5, 167.6, 168.1; Anal. Calcd. For C$_{22}$H$_{22}$N$_2$O$_7$: C, 61.97; H, 5.20; N, 6.57. Found: C, 62.01; H, 5.26; N, 6.43.

EXAMPLE 3

(3-(1,3-Dioxoisoindolin-2-yl)-3-(3-ethoxy-4-methoxyphenyl)propanoylamino)pentanoate (3-(1,3-Dioxoisoindolin-2-yl)-3-(3-ethoxy-4-methoxyphenyl)propanoylamino)pentanoate was prepared as described in Example 1 from 3-(1,3-dioxoisoindolin-2-yl)-3-(3-ethoxy-4-methoxyphenyl)propanehydroxamic acid (1.0 g, 2.6 mmol) and pentanoic anhydride (0.97 g, 5.2 mmol) in anhydrous acetonitrile (30 mL). The product was obtained as a white solid (0.45 g, 37%): mp, 200.0-201.5° C.; $^1$H NMR (DMSO-d6) δ 0.83 (t, J=7.3 Hz, 3H, CH$_3$), 1.25-1.33 (m, 2H, CH$_2$), 1.31 (t, J=6.8 Hz, 3H, CH$_3$), 1.33-1.48 (m, 2H, CH$_2$), 2.36 (t, J=7.2 Hz, 2H, CH$_2$), 3.10-3.20 (m, 2H, CH$_2$), 3.72 (s, 3H, CH$_3$), 4.02 (q, J=6.4 Hz, 2H, OCH$_2$), 5.67 (t, J=7.6 Hz, 1H, CH), 6.89-7.01 (m, 3H, Ar), 7.85 (s, 4H, Ar), 11.86 (s, 1H, NH); $^{13}$C NMR (DMSO-d6) δ 13.4, 14.6, 21.3, 26.3, 30.4, 49.7, 55.4, 63.7, 111.8, 112.2, 119.4, 123.1, 130.9, 131.2, 134.5, 147.7, 148.5, 166.6, 167.6, 170.8; Anal. Calcd. for C$_{25}$H$_{28}$N$_2$O$_7$: C, 64.09; H, 6.02; N, 5.98. Found: C, 63.89; H, 6.04; N, 5.81.

EXAMPLE 4

(3-(1,3-Dioxoisoindolin-2-yl)-3-(3-ethoxy-4-methoxyphenyl)propanoylamino)benzoate (3-(1,3-Dioxoisoindolin-2-yl)-3-(3-ethoxy-4-methoxyphenyl)propanoyiamino)benzoate was prepared as described in Example 1 from 3-(1,3-dioxoisoindolin-2-yl)-3-(3-ethoxy-4-methoxyphenyl)propanehydroxamic acid (1.0 g, 2.6 mmol) and phenylcarbonyl benzoate (1.18 g, 5.2 mmol) in anhydrous acetonitrile (30 mL). The product was obtained as a white solid (0.70 g, 55.1%): mp, 196.0-198.0° C.; $^1$H NMR (DMSO-d6) δ 1.33 (t, J=6.6 Hz, 3H, CH$_3$), 3.31-3.46 (m, 2H, CH$_2$), 3.74 (s, 3H, OCH$_3$), 4.03 (q, J=6.4 Hz, 2H, OCH$_2$), 5.72 (t, J=7.5 Hz, 1H, CH), 6.94-7.07 (m, 3H, Ar), 7.50-8.00 (m, 9H, Ar), 12.20 (s, 1H, NH); $^{13}$C NMR (DMSO-d6) δ 55.5, 63.7, 111.8, 112.2, 119.4, 123.2, 126.6, 129.0, 129.4, 131.0, 131.2, 134.3, 134.6, 147.7, 148.6, 163.8, 167.0, 167.6; Anal. Calcd. for C$_{27}$H$_{24}$N$_2$O$_7$: C, 65.42; H, 5.10; N, 5.61. Found: C, 65.10; H, 4.90; N, 5.49.

EXAMPLE 5

(3-(3-Cyclopentyloxy-4-methoxyphenyl)-3-(1-oxoisoindolin-2-yl)propanoylamino)acetate (3-(3-Cyclopentyloxy-4-methoxyphenyl)-3-(1-oxoisoindolin-2-yl)propanoylamino)acetate was prepared by the general procedure A from 3-(3-cyclopentyloxy-4-methoxyphenyl)-3-(1-oxoisoindolin-2-yl)propanehydroxamic acid (2.86 g, 7.0 mmol) and acetic anhydride (1.42 g, 14.0 mmol) in anhydrous acetonitrile (110 mL). The product was obtained as a white solid (0.79 g, 27%): mp, 166.0-168.5° C.; $^1$H NMR (DMSO-d6) δ 1.50-1.82 (m, 8H, C$_5$H$_8$), 2.09 (s, 3H, CH$_3$), 3.04 (d, J=7.9 Hz, 2H CH$_2$), 3.71 (s, 3H, OCH$_3$), 4.17 (d, J=17.4 Hz, 1H, CHH,), 4.60 (d, J=17.4 Hz, 1H, CHH), 4.69-4.75 (m, 1H, OCH), 5.67 (t, J=7.8 Hz, 1H, CH), 6.83-6.93 (m, 3H, Ar), 7.45-7.70 (m, 4H, Ar), 11.86 (s, 1H, NH); $^{13}$C NMR (DMSO-d6) δ 17.9, 23.5, 32.1, 34.6, 51.0, 55.5, 79.5, 112.2, 113.9, 119.1, 122.8, 123.4, 127.8, 131.3, 131.6, 132.2, 141.7, 146.9, 149.1, 166.6, 167.0, 168.3; Anal. Calcd. for C$_{25}$H$_{28}$N$_2$O$_6$: C, 65.06; H, 6.33; N, 6.07. Found: C, 65.3; H, 6.26; N, 5.85.

EXAMPLE 6

(3-[4-(Acetylamino)-1,3-dioxoisoindolin-2-yl]-3-(3-ethoxy-4-mathoxyphenyl)propanoylamino)acetate (3-[4-(Acetylamino)-1,3-dioxoisoindolin-2-yl]-3-(3-ethoxy-4-methoxyphenyl)propanoylamino)acetate was prepared by the procedure of Example 1 from N-[2-[2-(N-hydroxycarbamoyl)-1-(3-ethoxy-4-methoxyphenyl)ethyl]-1,3-dioxoisoindolin-4-yl]acetamide (0.8 g, 1.8 mmol) and acetic anhydride(0.37 g, 3.6 mmol) in anhydrous acetonitrile (30 mL). The product was isolated as a white solid (0.55 g, 62.8%): mp, 279.0-280.0° C.; $^1$H NMR (DMSO-d6) δ 1.31 (t, J=6.9 Hz, 3H, CH$_3$), 2.07 (s, 3H, CH$_3$), 2.19 (s, 3H, CH$_3$), 3.15-3.26 (m, 2H, CH$_2$), 3.72 (s, 3H, OCH$_3$), 3.97 (q, J =6.4 (q, J=6.4 Hz, 2H, OCH$_2$), 5.64 (t, J=7.7 Hz, 1H, CH), 6.90-6.99 (m, 3H, Ar), 7.56 (d, J=7.3 Hz, 1H, Ar), 7.78 (t, J=7.7 Hz, 1H, Ar), 8.45 (d, J=8.0 Hz, 1H, Ar), 9.71 (s, 1H, NH), 11.86 (s, 1H, NH); $^{13}$C NMR (DMSO-d6) δ 14.7, 17,9, 24.2, 33.8, 49.7, 55.5, 63.8, 11.8, 118.0, 119.4, 135.8, 136.4, 147.8, 166.6, 167.2, 168.2, 169.3; Anal. Calcd. for C$_{24}$H$_{25}$N$_3$O$_8$: C59.62; H, 5.21; N, 8.69. Found: C, 59.44; H, 5.08; N, 8.50.

EXAMPLE 7

(3-(3-Ethoxy-4-methoxyphenyl)-3-(4-methyl-1,3-dioxoisoindolin-2-yl)propanoylamino)acetate (3-(3-Ethoxy-4-methoxyphenyl)-3-(4-methyl-1,3-dioxoisoindolin-2-yl)propanoylamino)acetate was prepared by the procedure of Example 1 from 3-(3-ethoxy-4-methoxyphenyl)-3-(4-methyl-1,3-dioxoisoindolin-2-yl)propanehydroxamic acid (1.0 g, 2.6 mmol) and acetic anhydride(0.53 g, 5.2 mmol) in anhydrous acetonitrile (30 mL). The product was isolated as a white solid (0.5 g, 53.2%): mp, 124.0-126.0° C.; $^1$H NMR (DMSO-d6) δ 1.31 (t, J=6.8 Hz, 3H, CH$_3$), 2.07 (s, 3H, CH$_3$), 2.61 (s, 3H, CH$_3$), 3.15-3.35 (m, 2H, CH$_2$), 3.72 (s, 3H, OCH$_3$), 4.00 (q, J=6.4 Hz, 2H, OCH$_2$), 5.65 (t, J=7.7 Hz, 1H, NCH), 6.85-7.02 (m, 3H, Ar), 7.61-7.70 (m, 3H, Ar), 11.85 (s, 1H, NH); $^{13}$C NMR (DMSO-d6) δ 14.6, 16.9, 17.9, 33.8, 49.6, 55.4, 63.7, 111.8, 112.2, 119.4, 120.7, 127.8, 131.1, 131.6, 134,0, 136.6, 137.3, 147.7, 148.5, 166.6, 167.5, 168.1, 168.2; Anal. Calcd. for C$_{23}$H$_{24}$N$_2$O$_7$: C, 62.72; H, 5.49; N, 6.36. Found: C, 62.79; H, 5.35; N, 6.26.

EXAMPLE 8

(3-(3-Ethoxy-4-methoxyphenyl)-3-(5-methyl-1,3-dioxoisoindolin-2-yl)propanoylamino)acetate (3-(3-Ethoxy-4-methoxyphenyl)-3-(5-methyl-1,3-dioxoisoindolin-2-yl)propanoylamino)acetate was prepared analogously to Example 1 from 3-(3-ethoxy-4-methoxyphenyl)-3-(5-methyl-1,3-dioxoisoindolin-2-yl)propanehydroxamic acid (0.90 g, 2.4 mmol) and acetic anhydride (0.48 g, 4.7 mmol) in anhydrous acetonitrile (27 mL). The product was obtained as a white solid (0.30 g, 30.0%): mp, 145.0-147.0° C.; $^1$H NMR (DMSO-d6) δ 1.31 (t, J=6.9 Hz, 3H, CH$_3$), 2.07 (s, 3H, CH$_3$), 2.48 (s, 3H, CH$_3$), 3.20-3.36 (m, 2H, CH$_2$), 3.72 (s, 3H, OCH$_3$), 4.00 (q, J=6.4 Hz, 2H, OCH$_2$), 5.65 (t, J=7.2 Hz, 1H, CH), 6.89-7.00 (m, 3H, Ar), 7.62-7.76 (m, 3H, Ar), 11.84 (s, 1H, NH); $^{13}$C NMR (DMSO-d6) δ 14.6, 17.9, 21.3, 33.9, 49.7, 55.4, 63.7, 111.8, 112.1, 119.3, 128.6, 131.1, 131.6, 134.9, 145.5, 147.7, 148.5, 166.6, 167.6, 167.7, 168.1; Anal. Calcd. for C$_{23}$H$_{24}$N$_2$O$_7$: C, 61.50; H, 5.36; N, 6.07. Found: C, 61.52; H, 5.46; N, 6.21.

EXAMPLE 9

(3-(3-Cyclopentyloxy-4-methoxyphenyl)-3-(4-methyl-1,3-dioxoisoindolin-2-yl)propanoylamino)acetate (3-(3-Cyclopentyloxy-4-methoxyphenyl)-3-(4-methyl-1,3-dioxoisoindolin-2-yl)propanoylamino)acetate was prepared analogously to Example 1 from 3-(3-cyclopentyloxy-4-methoxyphenyl)-3-(4-methyl-1,3-dioxoisoindolin-2-yl)propanehydroxamic acid (1.5 g, 3.4 mmol) and acetic anhydride (0.7 g, 6.8 mmol) in anhydrous acetonitrile (45 mL). The product was obtained as a white solid (0.61 g, 43.3%): mp, 150.0-152.0° C.; $^1$H NMR (DMSO-d6) δ 1.55-1.89 (m, 8H, C$_5$H$_8$), 2.08 (s, 3H, CH$_3$), 2.61 (s, 3H, CH$_3$), 3.22-3.36 (m, 2H, CH$_2$), 3.71 (s, 3H, OCH$_3$), 4.50-4.74 (m, 1H, OCH), 5.65 (t, J=7.5 Hz, 1H CH), 6.89-7.02 (m, 3H, Ar), 7.58-7.70 (m, 3H, Ar), 11.86 (s, 1H, NH); $^{13}$C NMR (DMSO-d6) δ 17.0, 17.9, 23.5, 32.1, 33.9, 49.6, 55.5, 79.6, 112.1, 114.0, 119.4, 120.7, 127.8, 131.1, 131.6, 134.0, 136.6, 137.3, 146.7, 149.2, 166.6, 167.5, 168.1, 168.3; Anal. Calcd. for C$_{26}$H$_{28}$N$_2$O$_7$: C, 64.25; H, 5.82; N, 5.75. Found: C, 64.13; H, 5.72; N, 5.55.

EXAMPLE 10

(3-(3-Cyclopentyloxy-4-methoxyphenyl)-3-(5-methyl-1,3-dioxoisoindolin-2-yl)propanoylamino)acetate (3-(3-Cyclopentyloxy-4-methoxyphenyl)-3-(5-methyl-1,3-dioxoisoindolin-2-yl)propanoylamino)acetate was prepared by the procedure of Example 1 from 3-(3-cyclopentyloxy-4-methoxyphenyl)-3-(5-methyl-1,3-dioxoisoindolin-2-yl)propanehydroxamic acid (1.0 g, 2.3 mmol) and acetic anhydride(0.47 g, 4.6 mmol) in anhydrous acetonitrile (30 mL). The product was obtained as a white solid (0.53 g, 48.5%): mp, 98.0-101.0° C.; $^1$H NMR (DMSO-d6) δ 1.50-1.95 (m, 8H, C$_5$H$_8$), 2.07 (s, 3H, CH$_3$), 2.50 (s, 3H, CH$_3$), 3.10-3.26 (m, 2H, CH$_2$), 3.70 (s, 3H, OCH$_3$), 4.60-4.80 (m, 1H, OCH), 5.64 (t, J=7.7 Hz, 1H, CH), 6.88-7.01 (m, 3H, Ar), 7.61-7.76 (m, 3H, Ar), 11.86 (s, 1H, NH); $^{13}$C NMR (DMSO-d6) δ 17.9, 21.3, 23.5, 32.1, 33.9, 49.8, 55.5, 79.5, 112.1, 113.9, 119.4, 123.0, 123.5, 128.6, 131.0, 131.6, 134.9, 145.5, 146.7, 149.1, 166.6, 167.6, 167.7, 168.1; Anal. Calcd. for C$_{26}$H$_{28}$N$_2$O$_7$: C, 64.68; H, 5.90; N, 5.80. Found: C, 64.47; H, 5.81; N, 5.62.

EXAMPLE 11

(N-Acetyl-3-(3-ethoxy-4-methoxyphenyl)-3-(5-methyl-1,3-dioxoisoindolin-2-yl)propanoylamino)acetate (N-Acetyl-3-(3-ethoxy-4-methoxyphenyl)-3-(5-methyl-1,3-dioxoisoindolin-2-yl)propanoylamino)acetate was prepared by the procedure of Example 1 from 3-(3-ethoxy-4-methoxyphenyl)-3-(5-methyl-1,3-dioxoisoindolin-2-yl)propanehydroxamic acid (0.9 g, 2.3 mmol) and acetic anhydride (0.48 g, 4.7 mmol) in anhydrous acetonitrile (27 mL). The product was obtained as a white solid (0.06 g, 6%): mp, 128.0-129.5.° C.; $^1$H NMR (DMSO-d6) δ 1.30 (t, J=6.8 Hz, 3H, CH$_3$), 2.26 (s, 3H, CH$_3$), 2.28 (s, 3H, CH$_3$), 2.50 (s, 3H, CH$_3$), 3.55-4.15 (m, 2H, CH$_2$), 3.72 (s, 3H OCH$_3$), 4.00 (q, J=6.8 Hz, 2H, OCH$_2$), 5.67 (t, J=3.3 Hz, 1H, CH), 6.89-7.00 (m, 3H, Ar), 7.62-7.76 (m, 3H, Ar); $^{13}$C NMR (DMSO-d6) δ 14.6, 17.9, 21.3, 33.9, 49.7, 55.4, 63.7, 111.8, 112.1, 119.3, 128.6, 131.1, 131.6, 134.9, 145.5, 147.7, 148.5, 166.6, 167.6, 167.7, 168.1; Anal. Calcd. for C$_{25}$H$_{26}$N$_2$O$_8$: C, 62.23; H, 5.43; N, 5.81. Found: C, 61.83; H, 5.33; N, 5.53.

EXAMPLE 12

(N-Acetyl-3-(3-cyclopentyloxy-4-methoxyphenyl)-3-(4-methyl-1,3-dioxoisoindolin-2-yl)propanoylamino)acetate (N-Acetyl-3-(3-cyclopentyloxy-4-methoxyphenyl)-3-(4-methyl-1,3-dioxoisoindolin-2-yl)propanoylamino)acetate was prepared by the procedure of Example 1 from 3-(3-cyclopentyloxy-4-methoxyphenyl)-3-(4-methyl-1,3-dioxoisoindolin-2-yl)propanehydroxamic acid (1.5 g, 3.4 mmol) and acetic anhydride (0.7 g, 6.8 mmol) in anhydrous acetonitrile (45 mL). The product was obtained as a white solid (0.21 g, 12.8%): mp, 120.0-122.0° C.; $^1$H NMR (DMSO-d6) δ 1.50-1.90 (m, 8H, C$_5$H$_8$), 2.28 (s, 3H, CH$_3$), 2.29 (s, 3H, CH$_3$), 2.61 (s, 3H, CH$_3$), 3.71 (s, 3H, OCH$_3$), 3.50-4.10 (m, 2H, CH$_2$), 4.60-4.70 (m, 1H, OCH), 5.67 (t, J=8.9 Hz, 1H, CH), 6.80-7.10 (m, 3H, Ar), 7.50-7.75 (m, 3H, Ar); $^{13}$C NMR (DMSO-d6) δ 17.0, 17.7, 23.5, 23.6, 23.7, 32.1, 49.0, 55.5, 79.6, 112.2, 113.9, 119.3, 120.8, 127.6, 131.1, 131.5, 134.2, 136.8, 137.4, 146.8, 149.2, 167.6, 167.7, 168.3; Anal. Calcd. for C$_{28}$H$_{30}$N$_2$O$_8$: C, 64.36; H, 5.79; N, 5.36. Found: C, 64.40; H, 5.73; N, 5.04.

EXAMPLE 13

(3-[5-(Acetylamino)-1,3-dioxoisoindolin-2-yl]-3-(3-ethoxy-4-methoxyphenyl)propanoylamino)acetate (3-[5-(Acetylamino)-1,3-dioxoisoindolin-2-yl]-3-(3-ethoxy-4-methoxyphenyl)propanoylamino)acetate was prepared by the procedure of Example 1 from N-[2-[2-(N-hydroxycarbamoyl)-1-(3-ethoxy-4-methoxyphenyl)ethyl]-1,3-dioxoisoindolin-5-yl]acetamide (0.75 g, 1.7 mmol) and acetic anhydride (0.21 g, 2.0 mmol) in anhydrous acetonitrile (28 mL). The product was obtained as a white solid (0.60 g, 73%): mp, 178° C. (decomp.); $^1$H NMR (DMSO-d6) δ 1.31 (t, J=7.0 Hz, 3H, CH$_3$), 2.07 (s, 3H, CH$_3$), 2.12 (s, 3H, CH$_3$), 3.19 (dd, J=7.1, 15 Hz, 1H, CHH), 3.23-3.43 (m, 1H, CHH), 3.72 (s, 3H, CH$_3$), 3.98 (q, J=7.0 Hz, 2H, CH$_2$), 5.63 (t, J=8.5 Hz, 1H, CH), 6.89 (s, 2H, Ar), 7.00 (s, 1H, Ar), 7.77-7.86 (m, 2H, Ar), 8.17 (d, J=1.1 Hz 1H, Ar), 10.56 (br s, 1H, NH), 11.85 (br s, 1H, NH); $^{13}$C NMR (DMSO-d6) δ 14.6, 17.9, 24.2, 33.9, 49.8, 55.4, 63.7, 111.7, 112.1, 112.6, 119.3, 123.2, 124.3, 124.8, 131.1, 132.7, 144.8, 147.7, 148.5, 166.5, 167.2, 167.4, 168.1, 169.3; Anal. Calcd. for $C_{24}H_{25}N_3O_8$: C, 59.62; H, 5.21; N, 8.69. Found: C, 59.34; H, 5.30; N, 8.58.

EXAMPLE 14

(3-(1,3-Dioxobenzo[e]isoindolin-2-yl)-3-(3-ethoxy-4-methoxyphenyl)propanoylamino)acetate (3-(1,3-Dioxobenzo[e]isoindolin-2-yl)-3-(3-ethoxy-4-methoxyphenyl)propanoylamino)acetate was prepared by the procedure of Example 1 from 3-(1,3-dioxobeno[e]isoindolin-2-yl)-3-(3-ethoxy-4-methoxyphenyl)propanehydroxamic acid (1.0 g, 2.3 mmol), acetic anhydride (0.50 mL, 5.3 mmol) in acetonitrile (30 mL). The product was obtained as a yellow solid (135 mg, 12% yield): mp, 180° C. (decomp); $^1$H NMR (DMSO-$d_6$) δ 1.30 (t, J=6.9 Hz, 3H, $CH_3$), 2.04 (s, 3H, $CH_3$), 3.24 (dd, J=7.0, 15.1 Hz, 1H, CHH), 3.40 (dd, J=8.8, 15.1 Hz, 1H CHH), 3.71 (s, 3H, $CH_3$), 4.09 (q, J=7.1 Hz, 2H, $CH_2$), 5.72 (t, J=8.3 Hz, 1H NCH), 6.89-6.99 (m, 2H, Ar), 7.06 (s, 1H, Ar), 7.72-7.89 (m, 3H, Ar), 8.17 (d, J=8 Hz, 1H, Ar), 8.40 (d, J=8.3 Hz, 1H, Ar), 8.79 (d, J=8.2 Hz, 1H, Ar), 11.90 (brs, 1H, NH); $^{13}$C NMR (DMSO-$d_6$) δ 14.65, 17.87, 34.07, 43.73, 55.43, 63.71, 111.78, 112.20, 118.37, 119.38, 123.80, 126.22, 127.09, 128.79, 129.12, 129.81, 130.74, 131.11, 135.43, 136.16, 147.22, 148.52, 166.58, 168.05, 168.81; Anal Calcd for $C_{26}H_{24}N_2O_7$: C, 65.54; H, 5.08; N, 5.88. Found: C, 65.40; H, 5.27; N, 5.76.

EXAMPLE 15

(3-(3-Ethoxy-4-methoxyphenyl)-3-phthalimido-propanoylamino)pyridine-3-carboxylate (3-(3-Ethoxy-4-methoxyphenyl)-3-phthalimido-propanoylamino)pyridine-3-carboxylate was prepared analogously to Example 1 from 3-(3-ethoxy-4-methoxyphenyl)-3-phthalimido-N-hydroxypropionamide (768 mg, 2.0 mmol), triethyl amine (0.7 mL, 5.0 mmol) and nicotinoyl chloride hydrochloride (391 mg, 2.2 mmol) in anhydrous acetonitrile (30 mL). The product was isolated as a white solid (250 mg, 26% yield): mp, 156.0-158.0° C.; $^1$H NMR (DMSO-$d_6$) δ 1.32 (t, J=6.9 Hz, 3H, $CH_3$), 3.28-3.45 (m, 2H, $CH_2$), 3.73 (s, 3H, $CH_3$), 4.00 (q, J=6.9 Hz, 2H, $CH_2$), 5.71 (t, J=7.5 Hz, 1H, NCH), 6.92-6.93 (m, 2H, Ar), 7.05 (br s, 1H Ar), 7.59 (dd, J=4.8, 7.9 Hz, 1H, Ar), 7.82-7.90 (m, 4H, Ar), 8.28-8.32 (m, 1H, Ar), 8.86-8.88 (m, 1H, Ar), 9.06-9.07 (m, 1H, Ar), 12.32 (br s, 1H, NH); $^{13}$C NMR (DMSO-$d_6$) δ 14.66, 33.87, 49.77, 55.45, 63.74, 111.83, 112.24, 119.45, 122.96, 123.17, 124.16, 130.97, 131.22, 134.60, 137.17, 147.75, 148.63, 149.97, 154.56, 162.92, 167.04, 167.64; Anal Calcd for $C_{26}H_{23}N_3O_7$+0.17 $H_2O$: C, 63.40; H, 4.78; N, 8.53; $H_2O$, 0.62. Found: C, 63.05; H, 4.64; N, 8.20; $H_2O$, 0.62.

EXAMPLE 16

(3-[4-(Acetylamino)-1,3-dioxoisoindolin-2-yl]-3-(3-cyclopentyloxy-4-methoxyphenyl)propanoylamino)acetate (3-[4-(Acetylamino)-1,3-dioxoisoindolin-2-yl]-3-(3-cyclopentyloxy-4-methoxyphenyl)propanoylamino)acetate was prepared by the procedure of Example 1 from N-[2-[2-(N-hydroxycarbamoyl)-1-(3-cyclopentyloxy-4-methoxyphenyl)ethyl]-1,3-dioxoisoindolin-4-yl]acetamide (1.3 g, 2.7 mmol), acetic anhydride (0.51 mL, 5.4 mmol) in acetonitrile (45 mL). The product was obtained as a yellow solid (95 mg, 7% yield): mp, 97.0-99.5° C.; $^1$H NMR (DMSO-$d_6$) δ 1.55-1.85 (m, 8H, $C_5H_8$), 2.07 (s, 3H, $CH_3$), 2.19 (s, 3H, $CH_3$), 3.18-3.37 (m, 2H, $CH_2$), 4.74 (m, 1H, OCH), 5.64 (t, J=7.7 Hz, 1H, NCH), 6.91 (br s, 2H, Ar), 7.00 (s, 1H, Ar), 7.56 (d, J=7.2 Hz, 1H, Ar), 7.77 (t, J=8.0 Hz, 1H, Ar), 8.40-8.47 (m, 1H, Ar), 9.71 (br s, 1H, NH, Ar), 11.86 (brs, 1H, NH); $^{13}$C NMR (DMSO-$d_6$) δ 17.9, 23.5, 24.2, 32.1, 33.8, 49.7, 55.5, 79.6, 112.1, 114.0, 116.2, 117.9, 119.4, 125.8, 130.8, 131.4, 135.8, 136.1, 146.7, 149.2, 166.5, 167.1, 168.1, 169.2; Anal Calcd for $C_{27}H_{29}N_3O_8$: C, 61.94; H, 5.58; N, 8.03. Found: C, 61.59; H, 5,48; N, 7.88.

EXAMPLE 17

(N-Acetyl-3-[4-(acetylamino)-1,3-dioxoisoindolin-2-yl]-3-(3-cyclopentyloxy-4-methoxyphenyl)propanoylamino)acetate (N-Acetyl-3-[4-(acetylamino)-1,3-dioxoisoindolin-2-yl]-3-(3-cyclopentyloxy-4-methoxyphenyl)propanoylamino)acetate was prepared by the procedure of Example 1 from N-[2-[2-(N-hydroxycarbamoyl)-1-(3-cyclopentyloxy-4-methoxyphenyl)ethyl]-1,3-dioxoisoindolin-4-yl]acetamide (1.3 g, 2.7 mmol), acetic anhydride (0.51 mL, 5.4 mmol) in acetonitrile (45 mL). The product was obtained as a yellow solid (240 mg, 33% yield): mp, 93.0-95.0° C.; $^1$H NMR (DMSO-d6) δ 1.55-1.85 (m, 8H, $C_5H_8$), 2.19 (s, 3H, $CH_3$), 2.28 (s, 3H, $CH_3$), 2.30 (s, 3H, $CH_3$), 3.55-4.25 (m, 2H, $CH_2$), 4.74 (m, 1H, OCH), 5.68 (dd, J=2.8, 7.7 Hz, 1H, NCH), 6.91 (br s, 2H, Ar), 7.00 (s, 1H, Ar), 7.54-7.57 (m, 1H, Ar), 7.78 (t, J=7.6 Hz, 1H, Ar), 8.42-8.47 (m, 1H, Ar), 9.71 (br s, 2H, NH, Ar); $^{13}$C NMR (DMSO-$d_6$) δ 17.8, 23.6, 24.4, 32.0, 32.1, 49.0, 55.6, 79.6, 112.1, 114.2, 116.5, 117.6, 118.1, 126.0, 130.8, 131.3, 135.8, 136.3, 146.8, 149.2, 167.1, 167.6, 168.1, 168.5, 169.1, 169.2; Anal Calcd for $C_{29}H_{31}N_3O_9$: C, 61.59; H, 5.52; N, 7.43. Found: C, 61.59; H, 5,46; N, 7.46.

EXAMPLE 18

(3-(3-Ethoxy-4-methoxyphenyl)-3-(1-oxoisoindolin-2-yl)propanoylamino)acetate (3-(3-Ethoxy-4-methoxyphenyl)-3-(1-oxoisoindolin-2-yl)propanoylamino)acetate was prepared by the procedure of Example 1 from 3-(3-ethoxy-4-methoxyphenyl)-3-(1-oxoisoindolin-2-yl)propanehydroxamic acid (500 mg, 1.35 mmol) and acetic anhydride (0.26 mL, 1.8 mmol) in anhydrous acetonitrile (20 mL). The product was obtained as a white solid (480 mg, 86%): mp, 131.5-134.0° C.; $^1$H NMR (DMSO-d6); δ 1.29 (t, J=6.9 Hz, 3H, $CH_3$), 2.09 (s, 3H, $CH_3$), 3.04 (d, J=7.8 Hz, 2H, $CH_2$), 3.73 (s, 3H, $CH_3$), 3.97-4.04 (m, 2H, $CH_2$), 4.14 (d, J=17.5 Hz, 1H, NCHH), 4.58 (d, J=17.5 Hz, 1H, NCHH), 5.73 (t, J=7.8 Hz, 1H, NCH), 6.85-6.95 (m, 3H, Ar), 7.44-7.70 (m, 4H, Ar), 11.85 (s, 1H, NH); $^{13}$C NMR (DMSO-$d_6$) δ 14.64, 17.89, 34.62, 46.37, 51.02, 55.43, 63.73, 111.86, 112.13, 119.14, 122.79, 123.36, 127.79, 131.29, 131.59, 132.17, 141.70, 147.88, 148.46, 166.58, 166.89, 168.30; Anal Calcd for $C_{22}H_{24}N_2O_6$: C, 64.07; H, 5.87; N, 6.79. Found: C, 63.96; H, 5.87; N, 6.58.

EXAMPLE 19

Tablets, each containing 50 mg of (3-(1,3-dioxoisoindolin-2-yl)-3-(3-ethoxy-4-methoxyphenyl)propanoylamino) propanoate are prepared in the following manner:

| Constituents (for 1000 tablets) | |
| --- | --- |
| (3-(1,3-dioxoisoindolin-2-yl)-3-(3-ethoxy-4-methoxyphenyl)propanoylamino) propanoate | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 20

Tablets, each containing 100 mg of (3-(1,3-dioxoisoindolin-2-yl)-3-(3-ethoxy-4-methoxyphenyl)propanoylamino) propanoate can be prepared in the following manner:

| Constituents (for 1000 tablets) | |
| --- | --- |
| (3-(1,3-dioxoisoindolin-2-yl)-3-(3-ethoxy-4-methoxyphenyl)propanoylamino) propanoate | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 21

Tablets for chewing, each containing 75 mg of (3-(1,3-dioxoisoindolin-2-yl)-3-(3-ethoxy-4-methoxyphenyl)propanoylamino)propanoate can be prepared in the following manner:

| Composition (for 1000 tablets) | |
| --- | --- |
| (3-(1,3-dioxoisoindolin-2-yl)-3-(3-ethoxy-4-methoxyphenyl)propanoylamino) propanoate | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. (3-(1,3-dioxoisoindolin-2-yl)-3-(3-ethoxy-4-methoxyphenyl)propanoylamino)propanoate, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 22

Tablets, each containing 10 mg (3-(1,3-dioxoisoindolin-2-yl)-3-(3-ethoxy-4-methoxyphenyl)propanoylamino)propanoate can be prepared in the following manner:

| Composition (for 1000 tablets) | |
| --- | --- |
| (3-(1,3-dioxoisoindolin-2-yl)-3-(3-ethoxy-4-methoxyphenyl)propanoylamino) propanoate | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 23

Gelatin dry-filled capsules, each containing 100 mg of (3-(1,3-dioxoisoindolin-2-yl)-3-(3-ethoxy-4-methoxyphenyl)propanoylamino)propanoate can be prepared in the following manner:

| Composition (for 1000 capsules) | |
|---|---|
| (3-(1,3-dioxoisoindolin-2-yl)-3-(3-ethoxy-4-methoxyphenyl)propanoylamino) propanoate | 100.0 g |
| microcrystalline cellulose | 30.0 g |
| sodium lauryl sulfate | 2.0 g |
| magnesium stearate | 8.0 g |

The sodium lauryl sulfate is sieved into the (3-(1,3-dioxoisoindolin-2-yl)-3-(3-ethoxy-4-methoxyphenyl)propanoylamino)propanoate through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 24

A 0.2% injection or infusion solution can be prepared, for example, in the following manner:

| | |
|---|---|
| (3-(1,3-dioxoisoindolin-2-yl)-3-(3-ethoxy-4-methoxyphenyl)propanoylamino) propanoate | 5.0 g |
| sodium chloride | 22.5 g |
| phosphate buffer pH 7.4 | 300.0 g |
| demineralized water to | 2,500.0 mL |

(3-(1,3-Dioxoisoindolin-2-yl)-3-(3-ethoxy-4-methoxyphenyl)propanoylamino)propanoate is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

EXAMPLE 25

(3-(4-Acetylamino-1,3-dioxoisoindolin-2-yl)-3-(3-ethoxy-4-methoxyphenyl)propanoylamino)propanate (3-(4-Acetylamino-1,3-dioxoisoindolin-2-yl)-3-(3-ethoxy-4-methoxyphenyl)-propanoylamino)propanate was prepared by the procedure used for example 1 from 3-(4-acetylamino-1,3-dioxoisoindolin-2-yl)-3-(3-ethoxy-4-methoxyphenyl)propane-hydroxamic acid (1 g, 2.26 mmol) and propionic anhydride (0.59 g, 4.53 mmol) in anhydrous acetonitrile (30 mL). The product was obtained as a white solid (0.96 g, 87%): mp, 147-149° C.; $^1$H NMR (DMSO-d$_6$) δ 11.86 (s,1H), 9.70 (s,1H), 8.43 (d, J=8.4 Hz, 1H), 7.77 (t, J=7.7 Hz, 1H), 7.55 (d, J=7.3 Hz, 1H), 7.00-6.91 (m, 3H), 5.65 (t, J=7.5 Hz, 1H), 4.01 (q, J=6.9 Hz, 2H), 3.72 (s, 3H), 3.34-3.24 (m, 2H), 2.38 (q, J=7.5 Hz, 2H), 2.19 (s, 3H), 1.31 (t, J=7.0 Hz, 3H), 1.02 (t, J=7.4 Hz, 3H); $^{13}$C NMR (DMSO-d$_6$) δ 171.63, 169.19, 168.15, 167.09, 166.59, 148.61, 147.74, 136.40, 138.73, 131.41, 130.80, 125.75, 119.38, 117.95, 116.62, 112.24, 111.79, 63.77, 55.45, 49.62, 33.75, 24.25, 24.19, 14.66.8.68; Anal. Calcd. For $C_{25}H_{27}N_3O_8$: C, 60.36; H, 5.47; N, 8.45. Found: C, 60.26; H, 5.45; N, 8.39.

EXAMPLE 26

(3-(4-Acetylamino-1,3-dioxoisoindolin-2-yl)-3-(3-ethoxy-4-methoxyphenyl)propanoylamino)butanoate (3-(4-Acetylamino-1,3-dioxoisoindolin-2-yl)-3-(3-ethoxy-4-methoxyphenyl)-propanoylamino)butanoate was prepared by the procedure used for example 1 from 3-(4-acetylamino-1,3-dioxoisoindolin-2-yl)-3-(3-ethoxy-4-methoxyphenyl)-propanehydroxamic acid (1.0 g, 2.26 mmol) and butyric anhydride (0.72 g, 4.53 mmol) in anhydrous acetonitrile (30 mL). The product was obtained as a white solid (0.93 g, 80%): mp, 105-107° C.; $^1$H NMR (DMSO-d$_6$) δ 11.84 (s, 1H), 9.69 (s, 1H), 8.42 (d, J=7.5 Hz, 1H), 7.77 (t, J=7.6 Hz, 1H), 7.55 (d, J=7.2 Hz, 1H), 6.99-6.91 (m, 3H), 5.64 (t, J=7.5 Hz, 1H), 4.00 (q, J=7.0 Hz, 2H), 3.72 (s, 3H), 3.31-3.24 (m, 2H), 2.35 (t, J=7.2 Hz, 2H), 2.18 (s, 3H), 1.51 (q, J=7.3 Hz, 2H), 1.31 (t, J=7.0 Hz, 3H), 0.86 (t, J=7.4 Hz, 3H); $^{13}$C NMR (DMSO-d$_6$) δ 170.95, 169.18, 168.09, 166.60, 148.60, 147.73, 136.40, 135.74, 131.42, 130.80, 125.75, 119.36, 117.96, 116.63, 112.22, 111.79, 63.70, 55.46, 49.61, 33.79, 32.56, 24.19, 17.80, 14.66, 13.14; Anal. Calcd. For $C_{26}H_{29}N_3O_8$: C, 61.05: H, 5.71; N, 8.21. Found: C, 60.95; H, 5.73; N, 7.97

EXAMPLE 27

(3-(4-Acetylamino-1,3-dioxoisoindolin-2-yl)-3-(3-ethoxy-4-methoxyphenyl)propanoylamino)benzoate (3-(4-Acetylamino-1,3-dioxoisoindolin-2-yl)-3-(3-ethoxy-4-methoxyphenyl)-propanoylamino)benzoate was prepared by the procedure used for example 1 from 3-(4acetylamino-1,3-dioxoisoindolin-2-yl)-3-(3-ethoxy-4-methoxyphenyl)-propane-hydroxamic acid (1.0 g, 2.26 mmol) and benzoic anhydride (1.02 g, 4.52 mmol) in anhydrous acetonitrile (30 mL). The product was obtained as a white solid (1.05 g, 55%): mp, 150-152° C.; $^1$H NMR (DMSO-d$_6$) δ 12.19 (s, 1H), 9.71 (s, 1H), 8.44 (d, J=8.4 Hz, 1H), 7.96-7.52 (m, 7H), 7.04-6.91 (m, 3H), 5.70 (t, J=7.5 Hz, 1H), 4.03 (q, J=6.9 Hz, 2H), 3.74 (s, 3H), 3.44-3.28 (m, 2H), 2.19 (s, 3H), 1.32 (t, J=6.9 Hz, 3H); $^{13}$C NMR (DMSO-d$_6$) δ 169.20, 168.17, 167.13, 166.93, 163.87, 148.62, 147.75, 136.42, 135.76, 134.31, 131.44, 130.79, 129.38, 129.05, 126.60, 125.80, 119.39, 118.00, 116.67, 112.24, 111.81, 63.77, 55.47, 49.60, 33.77, 24.20, 14.67; Anal. Calcd. For $C_{29}H_{27}N_3O_8$: C, 63.85; H, 4.99; N, 7.70. Found: C, 63.86; H, 4.98; N, 7.45.

EXAMPLE 28

(3-(4-Acetylamino-1,3-dioxoisoindolin-2-yl)-3-(3-ethoxy-4-methoxyphenyl)propanoylamino)isobutanoate (3-(4-Acetylamino-1,3-dioxoisoindolin-2-yl)-3-(3-ethoxy-4-methoxyphenyl)-propanoylamino)isobutanoate was prepared by the procedure used for example 1 from 3-(4-acetylamino-1,3-dioxoisoindolin-2-yl)-3-(3-ethoxy-4-methoxyphenyl)-propanehydroxamic acid (1.0 g, 2.26 mmol) and isobutyric anhydride (0.72 g, 4.52 mmol) in anhydrous acetonitrile (30 mL). The product was obtained as a white solid (1.02 g, 87%): mp, 104-106° C.; $^1$H NMR (DMSO-$d_6$) δ 11.84 (s, 1H), 9.70 (s, 1H), 8.42 (d, J=8.4 Hz, 1H), 7.77 (t, J=7.5 Hz, 1H), 7.56 (d, J=7.2 Hz, 1H), 6.99-6.91 (m, 3H), 5.64 (t, J=7.5 Hz, 1H), 4.00 (q, J=7.0 Hz, 2H), 3.72 (s, 3H), 3.33-3.25 (m, 2H), 2.68-2.62 (m, 1H), 2.19 (s, 3H), 1.31 (t, J=7.0 Hz, 3H), 1.15-1.04 (m, 6H); $^{13}$C NMR (DMSO-$d_6$) δ 174.10, 169.18, 168.11, 167.06, 166.66, 148.60, 147.72, 136.40, 135.73, 131.40, 130.80, 125.77, 119.36, 117.96, 116.62, 112.24, 111.79, 63.75, 55.45, 49.54, 33.78, 31.20, 24.17, 18.58, 14.54; Anal. Calcd. For $C_{26}H_{29}N_3O_8$: C, 61.05; H, 5.71; N, 8.21. Found: C, 60.97; H, 5.83; N, 7.96.

We claim:

1. A pharmaceutical composition comprising:
(a) a compound of the formula:

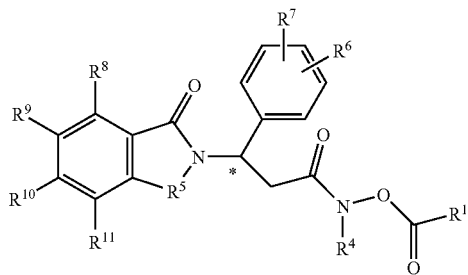

or an acid addition salts thereof,
wherein
the carbon atom designated * constitutes a center of chirality,
$R^4$ hydrogen or —(C═O)—$R^{12}$;
each of $R^1$ and $R^{12}$, independently of each other, is alkyl of 1 to 6 carbon atoms, phenyl, benzyl, pyridyl methyl, pyridyl, imidazoyl, imidazolylmethyl, or CHR*(CH$_2$)$_n$NR*R$^0$
wherein R* and $R^0$, independently of the other, are hydrogen, alkyl of 1 to 6 carbon atoms, phenyl, benzyl, pyridylmethyl, pyridyl, imidazoyl or imidazolylmethyl, and n=0, 1, 2;
$R^5$ is C═O, CH$_2$, —CH$_2$—CO—, or SO$_2$;
each of $R^6$ and $R^7$, independently of the other, is nitro, cyano, trifluoromethyl, carbethoxy, carbomethoxy, carbopropoxy, acetyl, carbamoyl, acetoxy, carboxy, hydroxy, amino, alkyl of 1 to 6 carbon atoms, alkoxy of 1 to 6 carbon atoms, cycloalkoxy of 3 to 8 carbon atoms, halo, bicycloalkyl of up to 18 carbon atoms, tricycloalkoxy of up to 18 carbon atoms, 1-indanyloxy, 2-indanyloxy, $C_4$-$C_8$-cycloalkylidenemethyl, or $C_3$-$C_{10}$-alkylidenemethyl; and each of $R^8$, $R^9$, $R^{10}$, and $R^{11}$ independently of the others, is
(i) hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, halo, or
(ii) one of $R^8$, $R^9$, $R^{10}$, and $R^{11}$ is acylamino comprising a lower alkyl, and the remaining of $R^8$, $R^9$, $R^{10}$, and $R^{11}$ are hydrogen, or
(iii) hydrogen if $R^8$ and $R^9$ taken together are benzo, quinoline, quinoxaline, benzimidazole, benzodioxole, 2-hydroxybenzimidazole, methylenedioxy, dialkoxy, or dialkyl, or
(iv) hydrogen if $R^{10}$ and $R^{11}$, taken together are benzo, quinoline, quinoxaline, benzimidazole, benzodioxole, 2-hydroxybenzimidazole, methylenedioxy, dialkoxy, or dialkyl, or
(v) hydrogen if $R^9$ and $R^{10}$ together are benzo; and
(b) a pharmaceutically acceptable carrier.

2. The pharmaceutical composition of claim 1, wherein said compound is a substantially chirally pure (R)-isomer or a substantially chirally pure (S)-isomer.

3. The pharmaceutical composition of claim 1, wherein the compound is (3-(1,3-dioxoisoindolin-2-yl)-3-(3-ethoxy-4-methoxyphenyl)propanoylamino)propanoate; (3-(1,3-dioxoisoindolin-2-yl)-3-(3-ethoxy-4-methoxyphenyl)propanoylamino)acetate; (3-(1,3-dioxoisoindolin-2-yl)-3-(3-ethoxy-4-methoxyphenyl)propanoylamino)pentanoate; (3-(1,3-dioxoisoindolin-2-yl)-3-(3-ethoxy-4-methoxyphenyl)propanoylamino)benzoate; (3-(3-cyclopentyloxy-4-methoxyphenyl)-3-(1-oxoisoindolin-2-yl)propanoylamino)acetate; (3-[4-(acetylamino)-1,3-dioxoisoindolin-2-yl]-3-(3-ethoxy-4-methoxyphenyl)propanoylamino)acetate; (3-(3-ethoxy-4-methoxyphenyl)-3-(4-methyl-1,3-dioxoisoindolin-2-yl)propanoylamino)acetate; (3-(3-ethoxy-4-methoxyphenyl)-3-(5-methyl-1,3-dioxoisoindolin-2-yl)propanoylamino)acetate; (3-(3-cyclopentyloxy-4-methoxyphenyl)-3-(4-methyl-1,3-dioxoisoindolin-2-yl)propanoylamino)acetate; (3-(3-cyclopentyloxy-4-methoxyphenyl)-3-(5-methyl-1,3-dioxoisoindolin-2-yl)propanoylamino)acetate; N-acetyl-(3-(3-ethoxy-4-methoxyphenyl)-3-(5-methyl-1,3-dioxoisoindolin-2-yl)propanoylamino)acetate; N-acetyl-(3-(3-cyclopentyloxy-4-methoxyphenyl)-3-(4-methyl-1,3-dioxoisoindolin-2-yl)propanoylamino)acetate; (3-[5-(acetylamino)-1,3-dioxoisoindolin-2-yl]-3-(3-ethoxy-4-methoxyphenyl)propanoylamino)acetate; (3-(1,3-dioxobenzo[e]isoindolin-2-yl)-3-(3-ethoxy-4-methoxyphenyl)propanoylamino)acetate; (3-(3-ethoxy-4-methoxyphenyl)-3-phthalimido-propanoylamino)pyridine-3-carboxylate; (3-[4-(acetylamino)-1,3-dioxoisoindolin-2-yl]-3-(3-cyclopentyloxy-4-methoxyphenyl)propanoylamino)acetate; (N-acetyl-3-[4-(acetylamino)-1,3-dioxoisoindolin-2-yl]-3-(3-cyclopentyloxy-4-methoxyphenyl)propanoylamino)acetate; or (3-(3-ethoxy-4-methoxyphenyl)-3-(1-oxoisoindolin-2-yl)propanoylamino)acetate.

4. The pharmaceutical composition of claim 3, wherein the compound is a substantially chirally pure (R)-isomer or a substantially chirally pure (S)-isomer.

5. A pharmaceutical composition comprising:
(a) a compound of the formula:

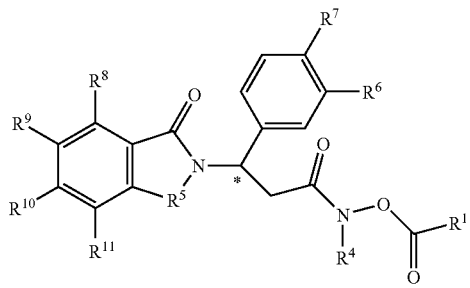

or an acid addition salt thereof,
in which
the carbon atom designated * constitutes a center of chirality;
$R^4$ is hydrogen or —(C=O)—$R^{12}$, where
  each of $R^1$ and $R^{12}$, independently of each other, is alkyl of 1 to 6 carbon atoms, phenyl, benzyl, pyridyl, pyridyl methyl, imidazolyl, imidazoylmethyl, or CHR*(CH$_2$)$_n$NR*R° wherein R* and R°, independently of the other, are hydrogen, alkyl of 1 to 6 carbon atoms, phenyl, benzyl, pyridylmethyl, pyridyl, imidazoyl or imidazolylmethyl, and n=0, 1, 2;
$R^5$ is C=O or CH$_2$;
each of $R^6$ and $R^7$, independently of the other is alkoxy of 1 to 8 carbon atoms, cycloalkoxy of 3 to 6 carbon atoms; $C_4$-$C_6$-cycloalkylidenemethyl, $C_2$-$C_{10}$-alkylidenemethyl, $C_6$-$C_{18}$-bicycloalkoxy, $C_6$-$C_{18}$-tricycloalkoxy, 1-indanyloxy, or 2-indanyloxy;
each of $R^8$, $R^9$, $R^{10}$, and $R^{11}$, independently of the others, is hydrogen, nitro, cyano, trifluoromethyl, carbethoxy, carbomethoxy, carbopropoxy, acetyl, halo, carbamoyl, acetoxy, carboxy, hydroxy, amino, alkylamino, dialkylamino, acylamino, alkyl of 1 to 10 carbon atoms, and alkoxy of 1 to 10 carbon atoms; and
(b) a pharmaceutically acceptable carrier.

6. The pharmaceutical composition of claim 5, wherein said compound is a substantially chirally pure (R)-isomer or a substantially chirally pure (S)-isomer.

* * * * *